United States Patent
Hayward et al.

[11] Patent Number: 6,071,535
[45] Date of Patent: *Jun. 6, 2000

[54] LIPID VESICLES FORMED WITH ALKYLAMMONIUM FATTY ACID SALTS

[75] Inventors: James A. Hayward, Stony Brook; David C. Watkins, Port Jefferson; Duncan T. Aust, Ridge, all of N.Y.

[73] Assignee: Collaborative Laboratories, Inc., East Setauket, N.Y.

[ * ] Notice: This patent is subject to a terminal disclaimer.

[21] Appl. No.: 09/255,160

[22] Filed: Feb. 22, 1999

Related U.S. Application Data

[63] Continuation-in-part of application No. 08/594,175, Jan. 31, 1996, Pat. No. 5,874,105.

[51] Int. Cl.[7] .......................... A61K 9/127; A61K 9/133; A61K 7/00

[52] U.S. Cl. .......................... 424/450; 424/401; 424/417; 424/70.1; 424/94.3; 264/4.1; 264/4.3; 514/880; 514/881; 935/54

[58] Field of Search .................................. 424/450, 1.21, 424/9.321, 9.51, 417, 70.1, 94.3; 264/4.1, 4.3, 4.6; 436/829; 935/54; 514/880, 881

[56] References Cited

U.S. PATENT DOCUMENTS

| | | |
|---|---|---|
| 2,650,165 | 8/1953 | Wahl . |
| 4,032,663 | 6/1977 | Kobayashi et al. . |
| 4,217,344 | 8/1980 | Vanlerberghe et al. . |
| 4,235,871 | 11/1980 | Papahadjopoulos et al. . |
| 4,247,411 | 1/1981 | Vanlerberghe et al. . |
| 4,342,826 | 8/1982 | Cole . |
| 4,483,921 | 11/1984 | Cole . |
| 4,485,054 | 11/1984 | Mezei et al. . |
| 4,533,254 | 8/1985 | Cook et al. . |
| 4,619,794 | 10/1986 | Hauser . |
| 4,663,167 | 5/1987 | Lopez-Berestein et al. . |
| 4,708,861 | 11/1987 | Popescu et al. . |
| 4,721,612 | 1/1988 | Janoff et al. . |
| 4,761,288 | 8/1988 | Mezei . |

(List continued on next page.)

FOREIGN PATENT DOCUMENTS

| | | |
|---|---|---|
| 0 158 441 A2 | 10/1985 | European Pat. Off. . |
| 0 561 424 B1 | 3/1997 | European Pat. Off. . |
| 57-82311 | 11/1980 | Japan . |

OTHER PUBLICATIONS

Hargreaves, W.R. et al., *Monoalkyl Liposomes* 17 (18):3759, 1978.

Kaler, E.W. et al., *Science* 245:1371, Sep. 22, 1989.

*Primary Examiner*—Gollamudi S. Kishore
*Attorney, Agent, or Firm*—Darby & Darby

[57] ABSTRACT

The present invention provides for liposomes formed with alkylammonium fatty acid salts, and methods for manufacturing same. The liposomes of the invention may deliver entrapped load material or materials at the occurrence of a preset triggering condition. Preferred liposomes of the invention are cationic liposomes. The preferred liposomes of the invention are formed with alkylammonium fatty acid salts, e.g., trialkylammonium fatty acid salts of long chain amides. The liposomes of the invention are used to encapsulate both hydrophobic and hydrophilic load materials. The liposomes formed accordingly are capable of delivering their loads upon the occurrence of a trigger or control condition.

25 Claims, 10 Drawing Sheets

U.S. PATENT DOCUMENTS

| | | |
|---|---|---|
| 4,812,312 | 3/1989 | Lopez-Berestein et al. . |
| 4,857,319 | 8/1989 | Crowe et al. . |
| 4,873,088 | 10/1989 | Mayhew et al. . |
| 4,888,288 | 12/1989 | Wagner . |
| 4,897,269 | 1/1990 | Mezei . |
| 4,908,154 | 3/1990 | Cook et al. . |
| 4,911,928 | 3/1990 | Wallach . |
| 4,978,654 | 12/1990 | Lopez-Berestein et al. . |
| 5,000,958 | 3/1991 | Fountain et al. . |
| 5,032,457 | 7/1991 | Wallach . |
| 5,128,139 | 7/1992 | Brown et al. . |
| 5,164,182 | 11/1992 | Meybeck et al. . |
| 5,165,994 | 11/1992 | Kaler et al. . |
| 5,190,764 | 3/1993 | Chiba et al. . |
| 5,262,310 | 11/1993 | Karube et al. . |
| 5,277,913 | 1/1994 | Thompson et al. . |
| 5,296,231 | 3/1994 | Yarosh . |
| 5,366,881 | 11/1994 | Singh et al. . |
| 5,443,839 | 8/1995 | Meybeck . |
| 5,466,467 | 11/1995 | Singh . |
| 5,585,109 | 12/1996 | Hayward et al. . |

LIPID VESICLES FORMED WITH ALKYLAMMONIUM FATTY ACID SALTS

This patent application is a continuation-in-part of U.S. patent application Ser. No. 08/594,175, filed Jan. 31, 1996, now U.S. Pat. No. 5,874,105, which is hereby incorporated herein by reference in its entirety.

BACKGROUND OF THE INVENTION

The present invention relates to the production of lipid vesicles (liposomes) and, more particularly, to the production of liposomes from long chain alkylammonium fatty acid salts.

Liposome formation is a natural result of the amphipathic nature of the molecules of which they are comprised. Amphipathic molecules are those molecules with distinct regions of the molecule having hydrophilic character and distinct regions of the same molecule having hydrophobic character. When dispersed in water, amphipathic molecules form three types of macro-molecular structure: micelles, hexagonal phase and lipid bilayers. The exact macromolecular structure which is formed depends on the relative sizes of the hydrophilic and hydrophobic regions of the molecule.

Micelle formation is favored when the cross sectional area of the hydrophilic region of the molecule is greater than that of the hydrophobic part of the molecule. Detergents are examples of such molecules, e.g., sodium palmitate. Detergents contain a hydrocarbon chain (the hydrophobic portion of the molecule) and an ionic base (the hydrophilic portion of the molecule), and act as emulsifying agents to bind water and oil phases. That is, detergents allow oil and water to be broken into tiny droplets suspended or dispersed in water. Particular detergents 1 may be classified as anions (negatively charged at the hydrophilic portion) and may be represented, as shown in FIG. 1, as having a hydrophilic head 2 with a hydrocarbon (hydrophobic) tail 4. FIG. 2 is a representation of a micelle structure 5 formed of a number of detergent molecules due to their hydrophilic/hydrophobic character.

In the opposite conformation, i.e., when the cross sectional area of the hydrophobic region of the molecule is greater than that of the hydrophilic part of the molecule, the formation of hexagonal phase structures is favored, e.g., dimyristoyl-phosphatidylethanolamine (DMPE). FIG. 4A is a representation of a hexagonal phase structure, sometimes referred to as an inverse micelle.

For molecules in which the cross sectional area of the hydrophilic region of the molecule is slightly less than, or equal to, that of the hydrophobic part of the molecule, such as many phospholipids, the formation of bilayers is favored, e.g., dipalmitoylphosphatidylcholine (DPPC). Phospholipids are an amphipathic type of lipid which contain phosphate, that is, molecules containing one phosphate, a glycerol and one or more fatty acids. FIG. 3 is a simplified representation of a phospholipid molecule 6, including a hydrophilic head 8 (i.e., the phosphate and glycerol) and a hydrophobic tail 10 (i.e., the one or more fatty acids). FIG. 4 is a representation of a phospholipid bylayer 12, where the hydrophobic regions 14 of the phospholipid molecules are caused to turn inward due to the aqueous environment, and the hydrophilic portions 16 face outward. These bilayers are two dimensional sheets in which all of the hydrophobic portions, e.g., acyl side chains, are shielded from interaction with water except those at the ends of the sheet. An energetically unfavorable interaction of the acyl chains with water results in the folding of the bilayers to form three-dimensional, vesicles. These vesicles are referred to as "liposomes".

Liposomes may be formed as a single bilayer enclosing a single aqueous space (small unilamellar vesicles; SUVS) or may be composed of concentric bilayers with many aqueous spaces alternating with the bilayers (multilamellar vesicles; MLVS). Liposomes can be used to encapsulate both hydrophobic and hydrophilic materials. Hydrophobic payloads are typically partitioned within the bilayers whereas hydrophilic payloads are typically trapped within the aqueous compartments. The advantages of using liposomes as a carrier/ encapsulation system is that they are stable and can protect their payload from degradation, e.g., by oxygen, digestive enzymes, etc.

For example, U.S. Pat. No. 3,957,971, issued May 15, 1976, discloses liposome-formed moisturizing units which are capable of moisturizing and improving flexibility, plasticity, and softness of keratinous matter, particularly mammalian skin. The liposomes within which the moisturizer is stored include a matrix of a ternary lipid mixture of lecithin, dicetyl phosphate, and a sterol, and include cavities disposed within the liposome. The cavities (lamellar space) contain an humectant, such as sodium pyroglutamate, in an aqueous medium. Moisturizing liposomes are also disclosed therein which function osmotically, serving as traps for water, which may be shared with the keratin constituents as required.

Liposomes also may be used for the timed delivery of a wide variety of materials including pharmaceuticals, cosmetics and nutrients. For example, U.S. Pat. No. 4,016,100, issued Apr. 5, 1977, discloses a method of producing a pharmaceutical composition comprised of an aqueous suspension of an active agent entrapped in a spherule of a phospholipid (liposome) The composition, or drug delivery vehicle, is prepared by dispersing a phospholipid uniformly in water to give an aqueous phospholipid dispersion, adding a medicament to the aqueous dispersion and freezing the thus-obtained aqueous dispersion to entrap the medicament in lipid spherules formed. The frozen dispersion is then thawed to realize an aqueous suspension of spherules having diameters of less than 5.0 microns. The timed release of an active agent is directly related to the amount of active agent trapped in the liposomes. The greater the amount of active agent, the longer the release process lasts.

A goal of the liposome research has been the development of a liposomal delivery system that would deliver its payload not over time as in the '100 patent mentioned above, but on cue, i.e., a controlled release, for example, in a mammalian body. For example, a delivery system that delivers its payload when applied to the skin or when arriving at a tumor. A bulk of the research has been based on admixtures of liposomes and other biological macromolecules such as antibodies and lecithins. Various degrees of success have been achieved with these systems but none have produced a liposome that will release its payload, or not, depending on the prevailing conditions. The invention described herein is just such a liposome: the degree of payload encapsulation may be altered by changes in pH and/or ionic strength of the surrounding medium thereby realizing a triggered delivery system in a form of a liposome.

SUMMARY OF THE INVENTION

It is therefore an object of the present invention to provide a lipid vesicle, or liposome, and method for manufacturing same, which overcomes the limitations of the prior art.

It is another object of the present invention to provide a liposome and method for manufacturing same which includes a controlled load delivery ability.

It is another object of the present invention to provide a liposome that is formed with an acyl $N_n,N_n$-dimethyl-1,n-diamino alkyl (ADDA) molecule, and method for manufacturing same.

It is another object of the present invention to provide a liposome which delivers its entrapped load at the occurrence of a preset condition, and method for inexpensively manufacturing same.

It is another object of the present invention to provide a liposome which displays cationic characteristics, and method for manufacturing same.

It is another object of the present invention to provide a liposome formed with alkylammonium fatty acid salts, e.g., trialkylammonium fatty acid salts, of long chain amides such that a portion of the molecular structure defined thereby includes a portion which readily adheres to protein and like molecules, and method for manufacturing same.

In one preferred embodiment, the present invention discloses a composition of matter, i.e., liposomes, for use in encapsulating both hydrophobic and hydrophilic substances (i.e., a "load"). The liposomes formed accordingly are capable of delivering their loads upon the occurrence of a trigger or control condition. For example, a liposome of this invention may stably encapsulate an active agent, genetic material or personal care element.

Upon being passed from an environment characteristic of a particular pH or temperature, their molecular structure becomes unstable in the changed environment causing the liposomes to deliver their load. Such a composition of matter, i.e., liposome, may be formed in accordance with the process or processes of manufacture disclosed herein. Such liposomes are marketed under the tradename CATEZOMES™.

CATEZOMES™ liposomes are prepared as follows: A fatty acid of between 12 and 28 carbon atoms is linked via an amide bond to a primary amino group of an $N_n$,$N_n$-dimethyl-1,n-diamino alkyl (DDA) chain, where n can be in a range of about 2 to 10. The fatty acid, e.g., behenic acid, is then linked to the DDA chain. The neutralized material formed thereby is an acyl $N_n$,$N_n$-dimethyl-1,n-diamino alkyl (ADDA) chain. The ADDA chain is then mixed with a fatty acid of between around 10 to 32 carbon atoms in equimolar proportions and at a pH of between around 5 to 11 such that a salt bond is formed between a quaternary amine group of the ADDA and a carboxyl group of the fatty acid. The result is an acyl ADDA (A-ADDA) salt. The salt bridge and the process of facilitating the same is key to the products formed thereby. The A-ADDA molecule formed is polar in the salt bond region, but typically carries a net charge of zero (zwitterionic). The alkyl chain region of the molecule is Hydrophobic. By altering the ratio of fatty acid to ADDA, the net surface charge of the liposome described hereby can be made anionic, cationic or neutral.

Preferably, the A-ADDA molecules are dispersed in water or any suitable buffering solution having a pH of around 5 to 11 and an ionic strength of less than about 1 molar NaCl. Dispersion is perfected either by using a mechanical homogenizer at ambient temperature or by stirring at a temperature above that of the melting point of the components of the mixture. Following the dispersion of the hydrocarbons in the buffer system, the mixture is subjected to high-sheer processing. Hydrophobic interactions between acyl chains form the A-ADDA molecules such that they take on a shape which is approximately cylindrical in cross section. The A-ADDA molecules, therefore, form bilayers, and liposomes, in aqueous solution. Accordingly, the stability of the liposomes is dependent upon the pH (changing) and/or ionic strength of solution. By decreasing the ratio of the Acyl:ADDA, a liposome which displays a cationic nature at the hydrophilic portion of the molecule is formed, i.e., a CATEZOMES™ liposome which displays powerful and useful binding abilities to proteins and like materials.

BRIEF DESCRIPTION OF THE DRAWINGS

FIG. 1 is a pictorial representation of a detergent molecule;

FIG. 2 is a pictorial representation of a micelle structure formed of a detergent molecule such as that represented in FIG. 1;

FIG. 3 is a pictorial representation of a phospholipid molecule;

FIG. 4 is a pictorial representation of a phospholipid bilayer;

FIG. 4A is a pictorial representation of a converted micelle;

FIG. 5 is an energy minimized molecular model of B-BDDP, produced by a molecular modeling program Insight II on a Silicon Graphics Indigo 4×24 work station.

FIG. 6 is a differential scanning calorimetry plot (thermogram) of P-PDDP Liposomes prepared as described in the text.

FIG. 7 is an image of a B-BDDP formed CATEZOMES™ liposomes the image formed by negative stain electroscopy, in accordance with the invention.

FIG. 8 is a plot of latency of a B-BDDP CATEZOMES™ liposomes formed in accordance herein; and FIG. 9 is a plot of latency of a B-BDDP CATEZOMES™ liposomes containing glucose.

FIG. 10 is a graphic representation of the preferential delivery of alpha bisabolol to the stratum corneum when encapsulated in CATEZOMES™ liposomes as compared to unencapsulated alpha bisabolol.

FIG. 11 is a graphic representation of the protection against UV damage offered by CATEZOMES™ liposomes containing organic sunscreens as measured by the change in free thiol groups (formation of disulphides) per unit weight of hair.

FIG. 12A is a graphic representation of the feel of a hair tress upon treatment with centrimonium chloride, CATEZOMES™ SI or water after rinse-out of the treatment.

FIG. 12B is a graphic representation of the feel of a hair tress upon treatment with centrimonium chloride, CATEZOMES™ SI or water after leave-in of the treatment.

FIG. 13A is a graphic representation of combing damage following treatment with centrimonium chloride, CATEZOMES™ SI or water after rinse-out of the treatment as measured by quantitation of proteins left on a comb when hair is either dry or wet.

FIG. 13B is a graphic representation of combing damage following treatment with centrimonium chloride, CATEZOMES™ SI or water after leave-in of the treatment as measured by quantitation of proteins left on a comb when hair is either dry or wet.

FIG. 14A is a graphic representation of the degree of fly-away upon combing following treatment with centrimonium chloride, CATEZOMES™ SI or water after rinse-out of the treatment as measured by hair spread in centimeters.

FIG. 14B is a graphic representation of the degree of fly-away upon combing following treatment with centrimonium chloride, CATEZOMES™ SI or water after leave-in of the treatment as measured by hair spread in centimeters.

DETAILED DESCRIPTION

Figure 1:
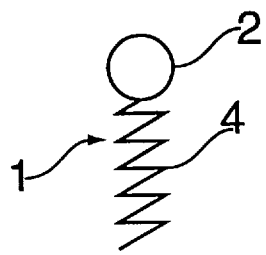
Figure 2:
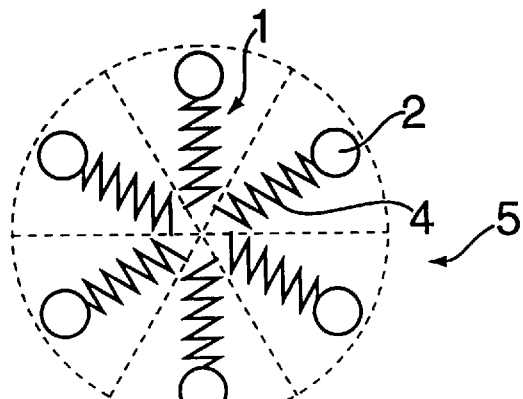
Figure 3:
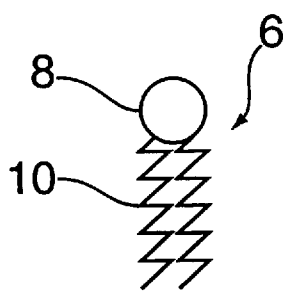
Figure 4:
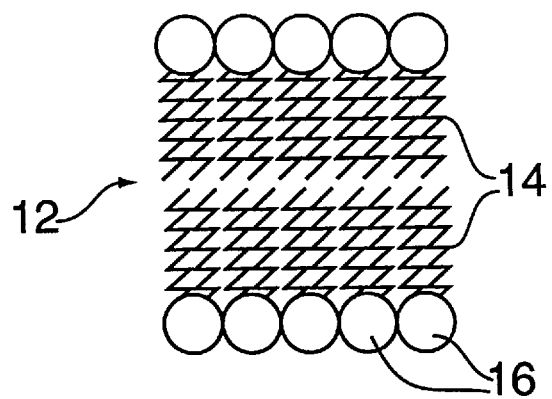
Figure 4A:
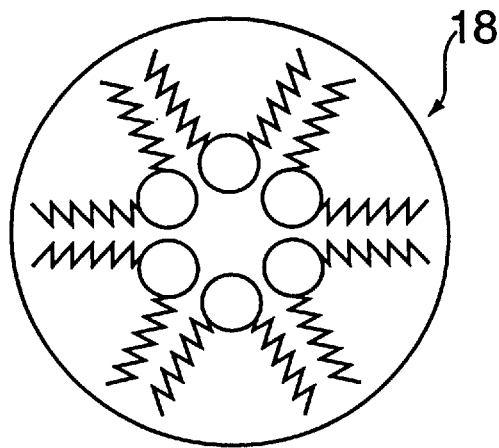

This invention relates to water-insoluble lipid vesicles (liposomes) prepared from alkylammonium fatty acid salts. While liposomes are not new, liposomes which can be inexpensively and efficiently formed and which display cationic characteristics as well as an ability to deliver their loads at the occurrence of a predetermined triggering condition are heretofore unknown. For example, U.S. Pat. No. 4,721,612, discloses a method and composition for the preparation of conventional lipid vesicles (liposomes) the bilayers of which comprise a salt form of an organic acid derivative of a sterol, such as the tris-salt form of a sterol hemisuccinate. The method disclosed therein allows for liposome formation which may be used to entrap compounds which are insoluble in aqueous solutions, such as bioactive agents of limited solubility. This conventionally formed liposome, however, includes no method for controlling delivery.

In contrast, liposomes of the present invention, because of their unique construction are highly sensitive to both pH and ionic strength of the surrounding medium in which they reside and are therefore specifically deliverable. This unique property results in part because they are formed of alkylammonium fatty acyl salts which are stabilized by a salt bridge. Such a characteristic provides the method to control the release of the load. The liposomes of the invention deliver their loads at the occurrence of a predetermined triggering condition. Examples of such triggering conditions include drying, heating, increased ionic strength and changes in pH. Preferably, the liposomes of this invention are formed with molecules which consist of the following parts: a fatty acid of between 12 and 28 carbon atoms; an $N_n,N_n$-dimethyl-1, n-diamino alkyl (DDA) chain with the number of carbons (n) being equal to 2–8, for example $N_3,N_3$-dimethyl-propyl-1,3-diamine [$NH_2(CH_2)_3N(CH_3)_2$]; and a fatty acid of between 10 and 30 carbon atoms, together forming the ADDA. To form its basic structure, one molecule of fatty acid is linked via an amide bond to the primary amino group of the DDA to form an acyl-DDA (ADDA), for example, behenyl-DDA or palmitol-DDA. Such ADDA material is available under the trade name Catemol from the Phoenix Chemical Co. of Somerville, N.J., i.e., Catemol 220 and 160, respectively.

When the fatty acid is behenic acid ($C_{22}$) and the DDA has 3 carbon atoms, the molecule would be $N_1$-behenamido-$N_2$, $N_2$-dimethyl-propyl-1,3-diamine [$CH_3(CH_2)_{20}CONHCH_2CH_2CH_2N(CH_3)_2$], (BDDP). Phoenix also sells another major group of chemicals which are a mixture of Catemol 220 and behenic acid, or Catemol 160 with palmitic acid to get Catemol 220B and 160P respectively. These are referred to herein as A-ADDAs (B-BDDP and P-PDDP). The ADDAs are cationic due to the quaternary amine; the A-ADDPs are inherently neutral. It should be noted that at pH less than about 10.5, the tertiary amine of the DDA will be protonated to form a quaternary amine with a positive charge. Free fatty acid carboxyl groups, attached to the tertiary amine group via the salt bridge, such as behenyl, have a pK of approximately 5 and so above a pH of 5 will be deprotonated and display a negative charge.

Figure 5:
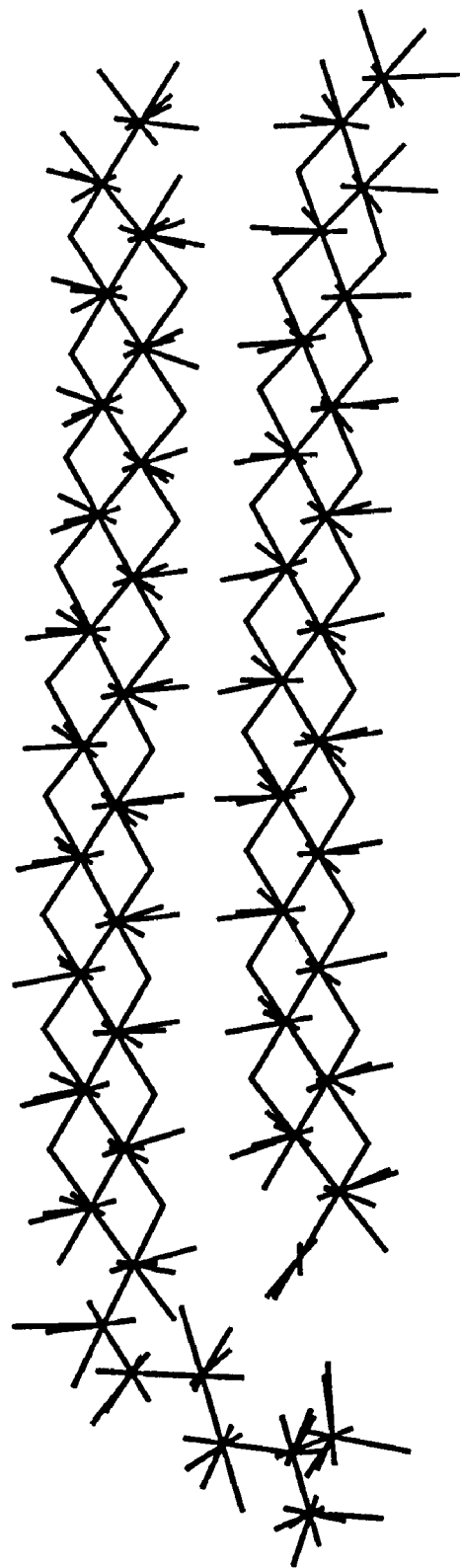

To form A-ADDAS, the ADDA is mixed with a second fatty acid of between 12 and 28 carbon atoms in equimolar proportions and at a pH between 6 and 10 such that a salt is formed between the quaternary amine group of the ADDA and the carboxyl group of the fatty acid to form acyl ADDA (A-ADDA). An example where the ADDA is BDDP and the first fatty acid is behenic acid (C22) would be behenyl-$N_1$-behenamido-$N_2,N_2$-dimethyl-propyl-1,3-diamine [$CH_3(CH_2)_{20}COO^-\cdot CH_3(CH_2)_{20}CONHCH_2CH_2CH_2N(CH_3)_2$], (B-BDDP). An energy minimized molecular model of B-BDDP is presented in FIG. 5. It is apparent from the molecular model shown in FIG. 5 that these molecules are amphipathic: the salt bond region of the molecule being polar, the alkyl chain region of the molecule being hydrophobic. The molecule is also approximately cylindrical in cross-section and thus would be predicted to form bilayers and liposomes in aqueous media as described above.

The long chain (greater than twelve carbons) A-ADDA is dispersed in a suitable vehicle (water or any aqueous solution having a pH range between 4.5 and 10.5 and an ionic strength of less than, or equivalent to 1 molar NaCl) either by using a mechanical homogenizer at ambient temperature or by stirring at a temperature above that of the melting point of the components of the mixture. Following dispersion of the hydrocarbons in the vehicle, the mixture is subjected to high-sheer processing. The precise conditions for the high-sheer processing step must be established empirically for each mixture.

In this context, high-sheer processing refers to any technique which is capable of mixing ingredients (liquid, solid or mixtures of both) in such a manner that significant energy is imparted to the mixture. Examples would include sonnicators, high-speed mixers and microfluidizers, which are conventional. In particular, U.S. Pat. Nos. 4,533,254 and 4,908,154, disclose conventional methods and apparatus for forming emulsions, a term used to include microemulsions, which could be utilized herein. A sheet within an emulsion-forming liquid mixture is forced under pressure to impinge upon itself in a low-pressure turbulent zone of the liquid utilizing an apparatus comprising a plurality of nozzles with elongated orifices for ejecting, under pressure, sheets of the emulsion-forming liquid. The jets are arranged to effect impingement of the sheets along a common liquid jet interaction front, thereby imposing mechanical energy. Such devices offer great flexibility in choice and amounts of immiscible liquids and emulsifying agents.

Similarly, mixing ADDA with a long chain alcohol (Cl2, C28), e.g., behenyl alcohol, will also result in a molecule with cylindrical cross-section. In this case, however, the cationic charge of the DDA is not neutralized and the liposomes which are formed have a large cationic surface charge.

The liposomes of the invention are used for encapsulating both hydrophobic and hydrophilic substances (i.e., a "load material"). Examples of such hydrophobic and hydrophilic materials include an water, active agent, genetic material or a personal care element.

As used herein, "genetic material" is defined as genetic material, specifically DNA/RNA oligonucleotides, genes, gene fragments and the like, and combinations thereof.

As used herein, "personal care element" is defined as water, a skin active, a hair active and a fragrance.

As used herein, a "skin active" is defined as any agent which exerts an effect on the skin. Examples of such skin actives used to encapsulate into the liposomes of the invention include water, organic sunscreens, pesticides, fragrances, oils, moisturizers e.g. alpha bisabolol, self-tanning agents, vitamin A derivatives, alpha hydroxy acids, beta hydroxy acids, topical anaesthetics, non-steroidal and steroidal anti-inflammatories, botanical extracts, proteins e.g. enzymes, known irritants including capsicum and it's derivatives, and combinations of said skin actives thereof.

As used herein, a "hair active" is defined as any agent which exerts an effect on the hair. Examples of such hair actives used to encapsulate into the liposomes of the invention include water, organic sunscreens, fragrances, oils, moisturizers, conditioners, silicones e.g. cyclomethicones, dimethicones and dimethiconols, pesticides e.g. those used in the treatment of lice infestations, proteins e.g. enzymes, including those used in the treatment of lice infestations and combinations of hair skin actives thereof.

EXAMPLE 1

B-BDDP is dispersed in phosphate-buffered saline (PBS: 20 mM phosphate buffer (pH 7.2) containing 140 mM NaCl) by stirring at a temperature of 70° C. for 20 minutes. The dispersion is then subjected to high-sheer processing by passage through a microfluidizer (Microfluidics, Newton, Mass.) five times, occurring at an operating pressure of 10,000 psi and an operating temperature between 10° C. and 20° C. It should be noted that any materials) to be incorporated into the liposomes are added either at the initial mixing stage or immediately prior to high-shear processing. It should be noted that the above process is also applicable to the production of CATEZOMES™ liposomes using other A-ADDA's, including, S-SDDP and P-PDDP.

Figure 6:
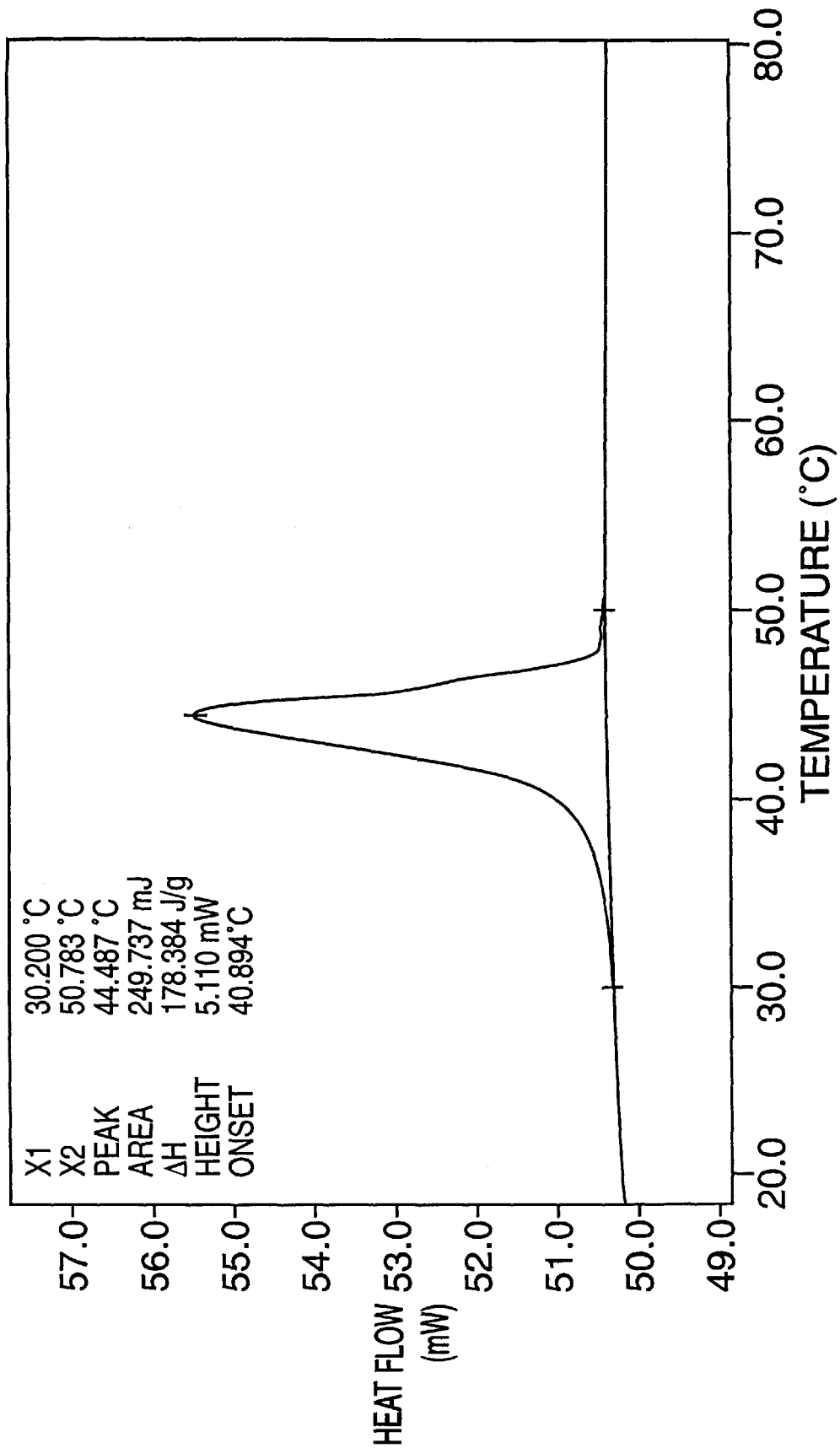
Figure 7:
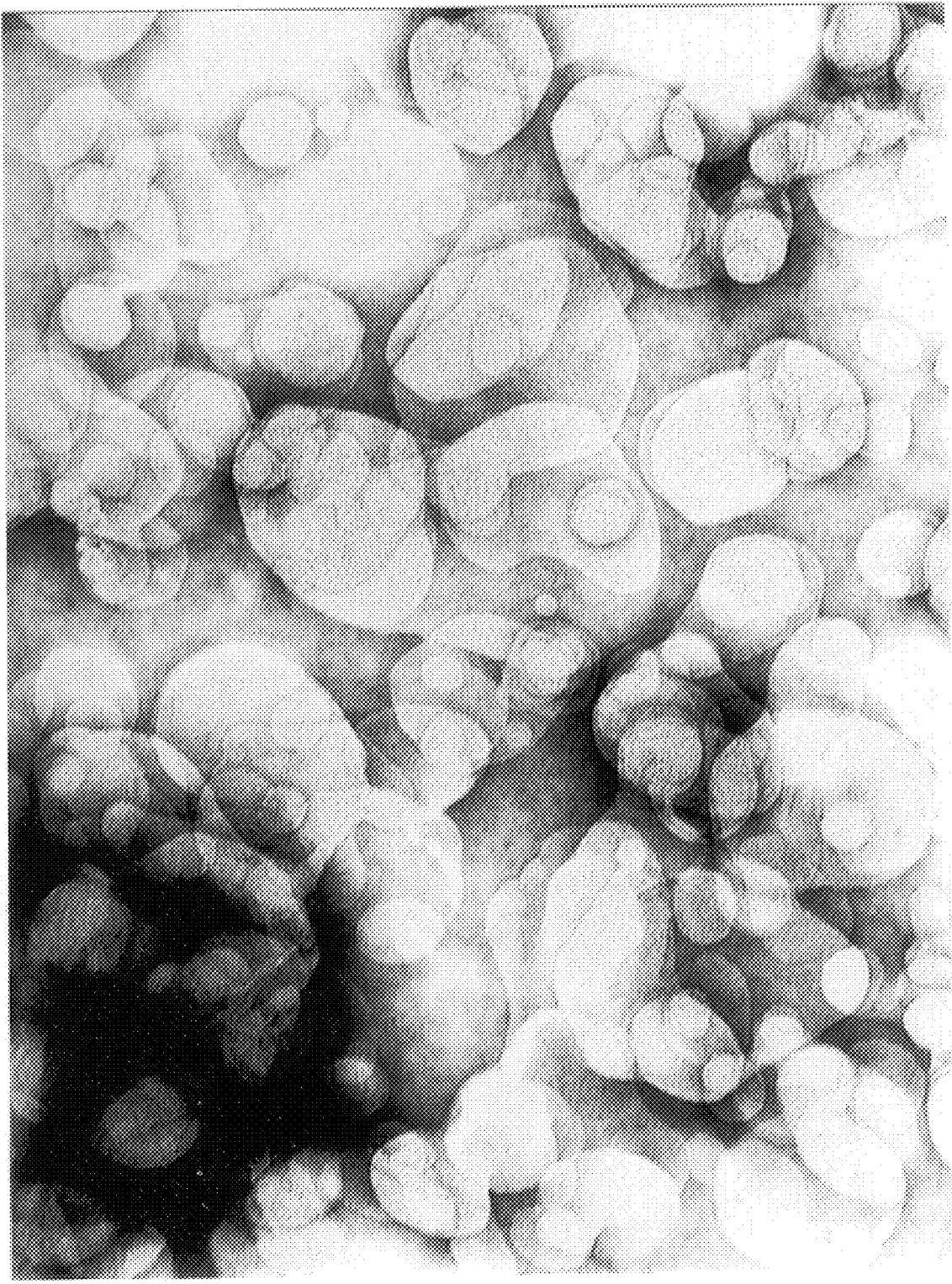

The integrity of the liposomes formed in accordance with Example 1 was affirmed using differential scanning calorimetry. The presence of a transition temperature characteristic of molecules in a liquid crystal arrangement, such as the alkyl chains of the liposome membranes, is shown in FIG. 6. Further demonstration of the formation of liposomes by B-BDDP is shown in a representative electron micrograph of FIG. 7.

The testing utilized to determine the payload efficiency of the CATEZOMES™ liposomes formed according to Example 1 is described in Example 2. In Example 2, Glucose was chosen as a model substance to examine the encapsulation capabilities of the subject liposomes because it is a low-molecular weight (180 g/mole), water-soluble, non-charged molecule. These characteristics make for the most difficulty in encapsulation for the following reasons. The low molecular weight means that even small, transient imperfections in the lipid membrane would permit leakage of the glucose from the vesicular space to the extra-vesicular space and thus the glucose will rapidly leave any but the most perfect liposomes. The fact that glucose is entirely water-soluble, lipid-insoluble means that there is no chance of the glucose partitioning into the lipid phase and therefore no "false encapsulation" will be apparent. Since the ADDAs have a positive charge due to the amine group, a negatively charged molecule would tend to be attracted to the membranes. Again this would be apparent as false encapsulation. Thus, although glucose is very difficult to encapsulate in liposomes, it constitutes the perfect test material to prove the existence of stable, flawless, enclosed vesicles.

EXAMPLE 2

Glucose was added to a Catemol 220B/buffer dispersion at a concentration of 10% w/w and then the CATEZOMES™ liposomes were formed as described above in Example 1. Non-encapsulated, i.e., extra-vesicular, glucose was then removed by placing the liposomes into a dialysis bag (molecular weight cut-off 5,000 daltons), placing the dialysis bag into a beaker of PBS (phosphate-buffered saline) and then replacing the PBS with freshly made PBS every two hours for a twenty-four hour period. The concentration of glucose in the extravesicular volume (unencapsulated glucose) was measured by assaying the glucose in a liposome suspension in the presence or absence of 10% (v/v) Octoxynol-9 detergent manufactured by Union Carbide Corporation, of Danbury Connecticut. Octoxynol-9 is a non-ionic detergent which disrupts the liposomes and permits the equilibration of glucose between intra- and extra-vesicular spaces. An assay kit, purchased from Sigma Chemical Company of St. Louis, Mo. (product number 115), was used according to the manufacturer's instructions. This assay is based on the, enzymatic conversion of glucose to glucose-6-phosphate with the concomitant reduction of nicotinamide dinucleotide phosphate (NADP) which can be detected spectrophotometrically. The absorption (520 nm) of the test sample is then extrapolated by comparison to a linear progression of standard (known) concentrations of glucose. Statistical analysis results of the slopes of these standard curves in the absence or presence of octoxynol-9 is presented in Table 1. These results assured that no interference from the detergent was apparent.

TABLE 1

| Statistical Analysis of Glucose Standard Curves | | |
|---|---|---|
| [Octoxynol-9] | 0% | 10% |
| n | 32 | 28 |
| Mean Slope | 0.249 | 0.262 |
| Standard Deviatian | 0.020 | 0.036 |

The concentration of glucose in the intravesicular volume (encapsulated glucose) is then determined by subtraction of the extra-vesicular glucose (measured in the absence of octyoxynol-9) from the total glucose (measured in the presence of octoxynol-9) (Equation 1).

$$[\text{Glucose}]_{inside} = [\text{Glucose}]_{total} - [\text{Glucose}]_{outside} \quad \text{Equation 1.}$$

In studies of liposomal encapsulation and stability, it is common to refer to "latency" which is the concentration of encapsulated payload expressed as a percentage of the total payload (Equation 2).

$$\text{Latency} = [\text{Glucose}]_{inside} + [\text{Glucose}]_{inside} \times 100 \quad \text{Equation 2.}$$

The concentration of intravesicular glucose is defined interchangeably herein, either in terms of concentration (mg/ml) or latency as defined above.

The encapsulation ability of liposomes made in accordance hereto, which are referred to interchangeably herein by their trade name CATEZOMES™ from various A-ADDAs in various vehicles was also compared. All the CATEZOMES™ liposomes were formed in accordance with Example 1 above-described. For comparison, "standard" or conventional liposomes, i.e., those made from a phospholipid, (DPPC),1,2-dipalmitoyl-sn-glycero-3- phosphocholine were also tested. The resulting data are summarized in Table 2. It is clear that no matter the chain length, all of the A-ADDAs formed as in Example 1 were shown to form sealed liposomes which encapsulated varying amounts of glucose. Furthermore, the process was clearly shown by the resulting data to be independent of the buffer system being used.

TABLE 2

Glucose Encapsulation by Liposomes of Various Composition
(Valued are in [Glc]in, mg/mL)

| Buffer | B-BDDP | S-SDDP | P-PDDP | DPPC |
|---|---|---|---|---|
| Tris-buffered Saline | 0.5 | 1.5 | ND | ND |
| Phosphate-Buffered Saline | 0.3 | 4.1 | 1.7 | 1.0 |
| Water | 0.3 | 3.9 | 1.9 | 1.0 |

Figure 8:
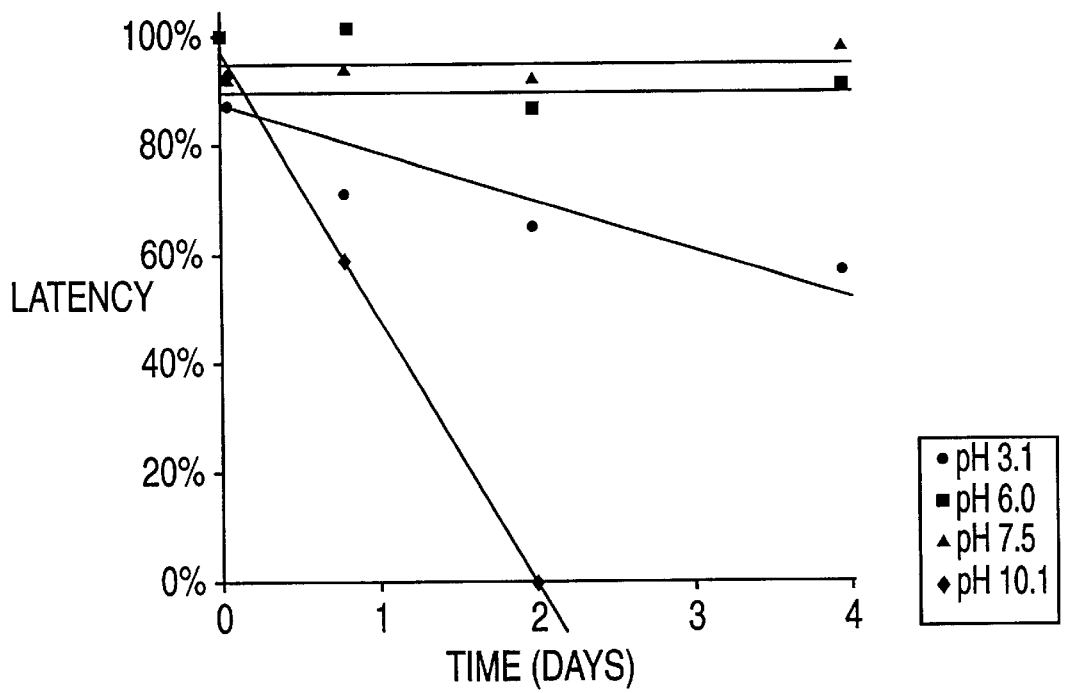

B-BDDP, behenyl-$N_1$-behenamido-$N_2,N_2$-dimethyl-propyl-1,3-diamine [$CH_3(CH_2)_{20}COO^- \cdot CH_3(CH_2)_{20}CONHCH_2CH_2CH_2N(CH_3)_2$]
S-SDDP, stearoyl-$N_1$-stearoylamido-$N_2,N_2$-dimethyl-propyl-1,3-diamine [$CH_3(CH_2)_{16}COO^- \cdot CH_3(CH_2)_{16}CONHCH_2CH_2CH_2N(CH_3)_2$]
P-PDDP, palmitoyl-$N_1$-palmitoylamido-$N_2,N_2$-dimethyl-propyl-1,3-diamine [$CH_3(CH_2)_{14}COO^- \cdot CH_3(CH_2)_{14}CONHCH_2CH_2CH_2N(CH_3)_2$]
DPPC, 1,2-dipalmitoyl-sn-glycero-3-phosphocholine; Tris-Buffered Saline, 20 mM Tris HCl, pH 7.2, 140 mM NaCl; Phosphate-Buffered Saline, 20 mM phosphate, pH 7.2, 140 mM NaCl; ND—not determined As mentioned above, the molecular shape of the A-ADDAS, which precipitates bilayer and liposome formation, is in part dependent on the salt bridge comprising the molecule. Concomitantly, the stability of the liposomes is dependent upon changing pH and/or ionic strength, which acutely affects the salt bridge. FIG. 8 shows the latency over time of B-BDDP liposomes prepared in buffers of various pH but identical ionic strength. The B-BDDP liposomes containing glucose were prepared as described above (Example 1.) Samples of these liposomes were then placed into phosphate buffers of various pH as shown, but with constant ionic strength. The latency (Equation 2) of the liposomes was then measured, as described in the text, at various times following the onset of the experiment.

Figure 9:
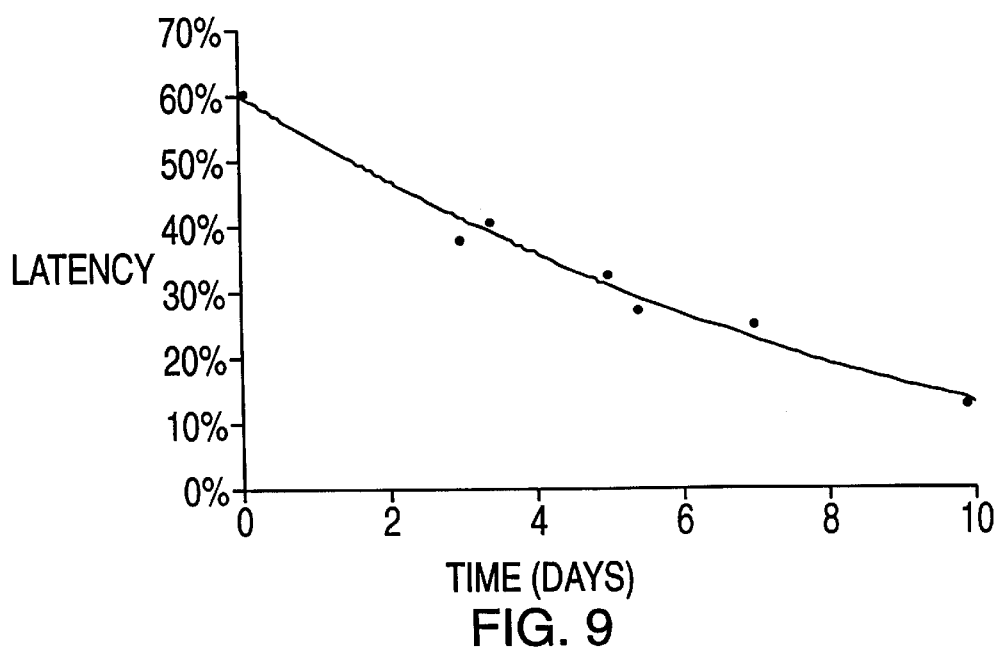

The measurement results clearly establish that the CATEZOMES™ liposomes are very stable at pH around neutrality, but become permeable to low molecular weight molecules such as glucose when the pH falls below 3 or increases above 10. This is entirely consistent with the notion that the salt bridge stabilizing the molecules is disruptable by pH. FIG. 9 shows the effect of increasing the ionic strength of the medium surrounding the CATEZOMES™ liposomes to 1.4 M NaCl. Clearly, the increased ionic strength disrupts the molecular structure of the B-BDDP and causes the liposomes to become permeable.

The experiments presented for B-BDDP in FIG. 8 and FIG. 9 were repeated for several other A-ADDAs and the data are presented in Table 3.

TABLE 3

Effects of pH and Ionic Strength on the Half-Life of A-ADDA Liposomes

|  | pH 3 | pH 10 | pH 7 | Hypertonic |
|---|---|---|---|---|
| B-BDDP | <3 days | <1 day | >1 month | <1 day |
| S-SDDP | <1 day | <1 day | >1 month | <1 day |
| P-PDDP | <1 day | <3 days | >1 month | <1 day |
| DPPC | 3 days | >1 month | >1 year | >1 year |

B-BDDP, behenyl-$N_1$-behenamido-$N_2,N_2$-dimethyl-propyl-1,3-diamine [$CH_3(CH_2)_{20}COO^- \cdot CH_3(CH_2)_{20}CONHCH_2CH_2CH_2N(CH_3)_2$]
S-SDDP, stearoyl-$N_1$-stearoylamido-$N_2,N_2$-dimethyl-propyl-1,3-diamine [$CH_3(CH_2)_{16}COO^- \cdot CH_3(CH_2)_{16}CONHCH_2CH_2CH_2N(CH_3)_2$]
P-PDDP, palmitoyl-$N_1$-palmitoylamido-$N_2,N_2$-dimethyl-propyl-1,3-diamine [$CH_3(CH_2)_{14}COO^- \cdot CH_3(CH_2)_{14}CONHCH_2CH_2CH_2N(CH_3)_2$]
DPPC, 1,2-dipalmitoyl-sn-glycero-3-phosphocholine

EXAMPLE 3

BDDP and a less than equimolar amount of Behenyl acid is dispersed in PBS along with lysozyme. The resulting CATEZOMES™ liposomes were found to display a cationic nature, and upon testing, found to bind readily to hair shafts and chitin shells of nits (eggs of head lice). Once the CATEZOMES™ liposomes are bound, surface interactions realize environmental characteristic changes, e.g., the result of the excretion of salts and/or acids by the skin or hair which cause payload release to begin and the lysozyme contacts and destroys the egg shell. Similarly, CATEZOMES™ liposomes formed in accordance hereto as containers for silicones were found to readily adhere to hair shafts for conditional delivery.

EXAMPLE 4

CATEZOMES™ liposomes of this invention as produced in Example 1 are used to deliver genetic material, specifically DNA/RNA oligonucleotides, genes, gene fragments and the like, to tissue culture cells, other cells in culture, airway epithelial cells, and topically to cells in the dermis via delivery down the sebaceous glands or hair follicles. In particular, the CATEZOMES™ liposomes of the invention were tested for their ability to facilitate transfection, i.e., the delivery of genetic material. Due to their cationic nature, the CATEZOMES™ liposomes formed thereby were able to deliver the gene for β-galactocidase to cells in culture and to airway epithelial cells in vivo.

EXAMPLE 5

CATEZOMES™ liposomes of the invention were produced as in Example 1 comprising 10% of a skin active hydrophobic material, alpha bisabolol (CATEZOMES™ B). These CATEZOMES™ B liposomes were formulated in water and found to be substantive to the stratum corneum of the skin. The CATEZOMES™ B liposomes formulation was applied to the volar forearm of volunteers. Tape strips were taken 5 minutes after application and again at 60 minutes after application of the test product. The alpha bisabolol was extracted form the tape strips and the amount of material assayed via HPLC. The results demonstrated that if alpha bisabolol is delivered as a solution in mineral oil, penetration and or loss of the active material from the upper layers of the stratum corneum begins within 5 minutes after application of the material. By sixty minutes after application, essentially all of the alpha bisabolol has penetrated to a depth below the ability of the assay to detect.

Figure 10:
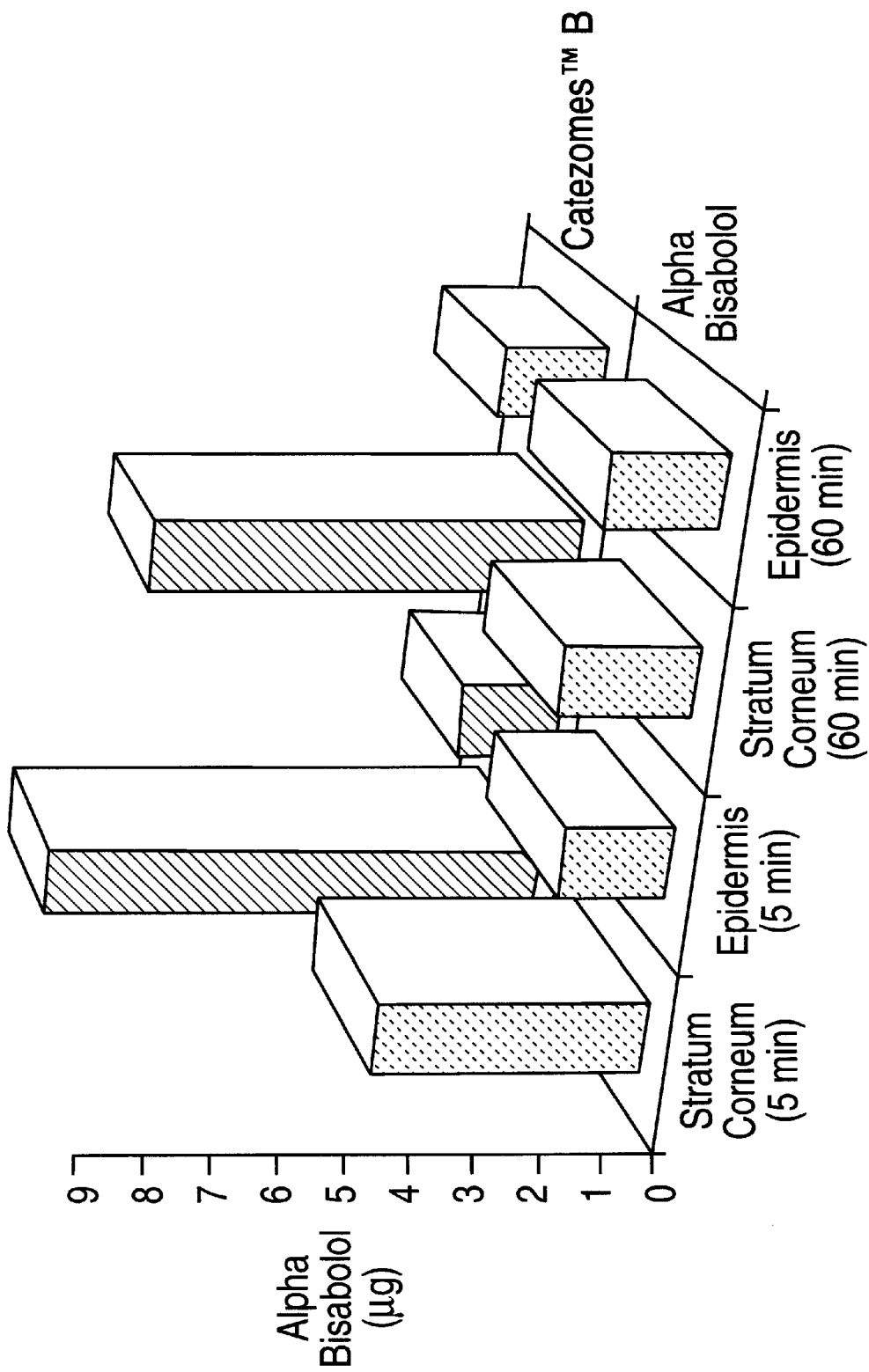

In sharp contrast, delivery of alpha bisabolol in the CATEZOMES™ B liposomes formulation system prevents loss of the alpha bisabolol from the surface and prevents penetration (FIG. 10). The CATEZOMES™ B liposomes of the invention may be formulated into any delivery vehicle which has a low ionic strength of less than about 1 molar NaCl in order to achieve this effect. The CATEZOMES™ liposome formulations of the invention are therefore ideally suited for the encapsulation of skin actives where penetration into the skin is not desirable and where sustained or protracted administration to the skin is desirable. Examples of such skin actives used to encapsulate into the liposomes of the invention include organic sunscreens, pesticides, fragrances, oils, moisturizers, self-tanning agents, proteins e.g. enzymes, known irritants including capsicum and it's derivatives, vitamin A derivatives, alpha hydroxy acids, beta hydroxy acids, topical anaesthetics, non-steroidal and steroidal anti-inflammatories and botanical extracts.

EXAMPLE 6

Figure 11:
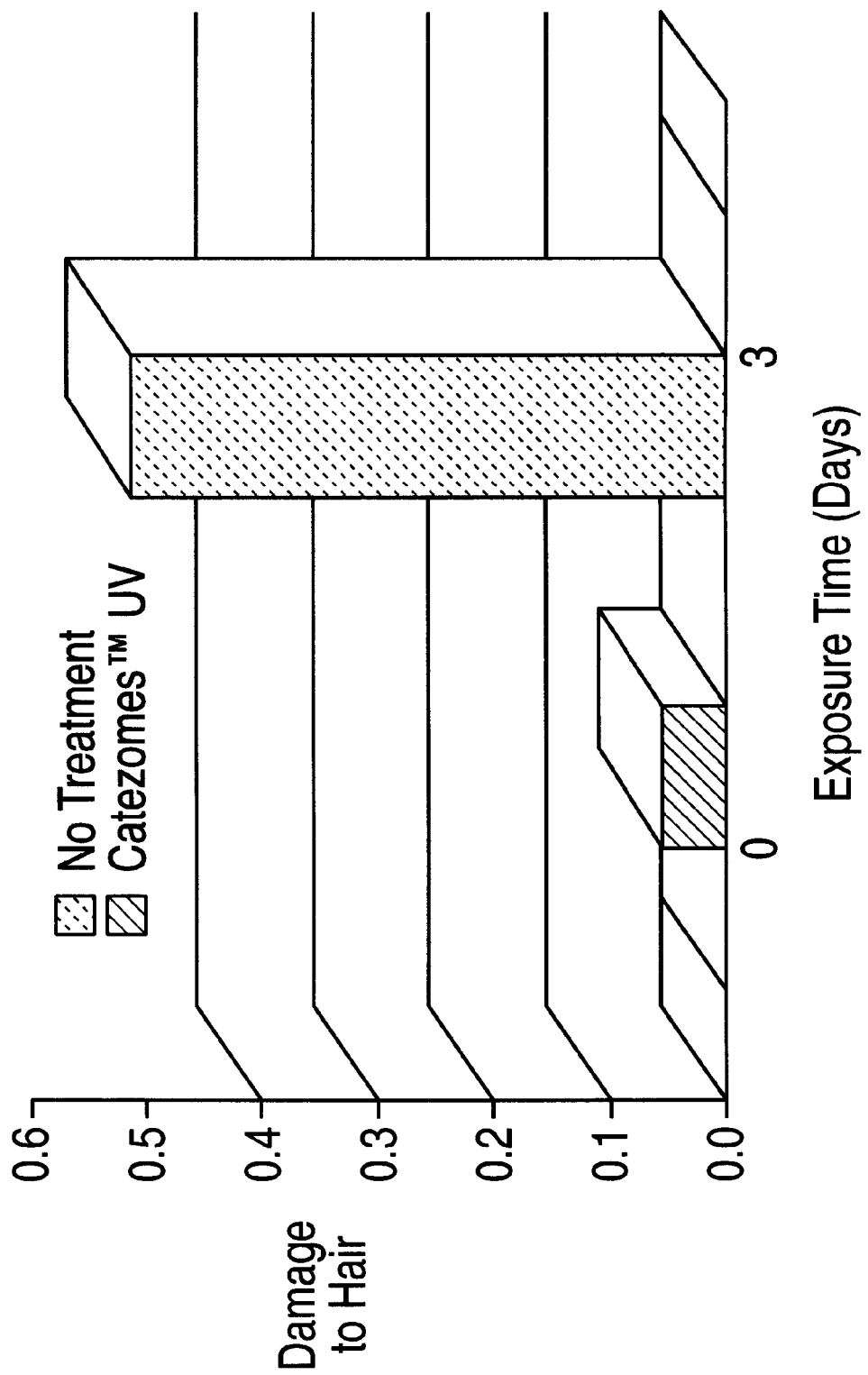

CATEZOMES™ liposomes of the invention were produced as in Example 1 containing 22.5% Octylmethoxy cinnamate (OMC) sunscreen and 15% Benzophenone 3 sunscreen and formulated into water. These CATEZOMES™ liposomes were shown to prevent the damage caused by UV radiation to the hair. The effects of UW irradiation on the disulphide cross-links within hair shafts was examined. FIG. 11 provides data showing damage to hair measured as the change in free thiol groups (formation of disulphides) per unit weight of hair over time (days). The data show that CATEZOMES™ liposomes containing organic sunscreens provide hair with substantial protection from UV damage.

In addition, by having substantivity to hair and skin it is believed that deposition of the liposomes of the invention which contain sunscreen material onto the surface of the stratum corneum may achieve higher SPF's than if the organic sunscreens were formulated in a conventional emulsion.

The CATEZOMES™ liposomes of the invention have been produced with a number of commonly used conventional organic sunscreens to achieve the same effect.

EXAMPLE 7

CATEZOMES™ liposomes of the invention were produced as in Example 1 containing 5% rose fragrance or 5% green floral fragrance. Such CATEZOMES™ liposomes were incorporated into dried or low water level fragrance products on their surfaces including the surfaces of kitty litter, such that fragrance release is suppressed until such time as the systems are activated by an increase in ionic concentration resulting from urination. Such an approach has been used in the development of a kitty litter that releases fragrance when urinated on by a cat and a deodorant product which releases fragrance upon sweating.

EXAMPLE 8

CATEZOMES™ liposomes of the invention were produced as in Example 1 containing 20% of the tanning agent dihydroxy acetone (DHA), an artificial tanning ingredient skin active, and formulated into water in order to ensure a more effective delivery of DHA to the stratum corneum and a more even and effective self tanning product.

EXAMPLE 9

CATEZOMES™ liposomes of the invention were produced as in Example 1 to contain 20% of each of the following silicone hair actives respectively: cyclomethicones, dimethicones and dimethiconols. These silicone hair active formulations have been shown to improve the feel of hair when used at levels below those of other conditioning agents such as centrimonium chloride.

In one embodiment, in order to show the effectiveness of such liposome formulations of the invention, a panel of six volunteers (3 male, 3 female) were asked to stroke hair tresses treated with conditioning agents and to rank the tresses according to how good the tresses felt. The CATEZOMES™ SI were formulated in water to give a final concentration of 0.25% (w/v) silicone. Two different hair tress samples was treated with the CATEZOMES™ liposomes formulation containing 20% dimethicone (CATEZOMES™ SI). This CATEZOMES™ SI formulation was compared to a formulation using the conventional conditioning agent centrimonium chloride formulated into water with a final concentration of 0.5% (w/v) centrimonium chloride. Following treatment, the hair tresses were either rinsed with water or left in the tress.

Figure 12B:
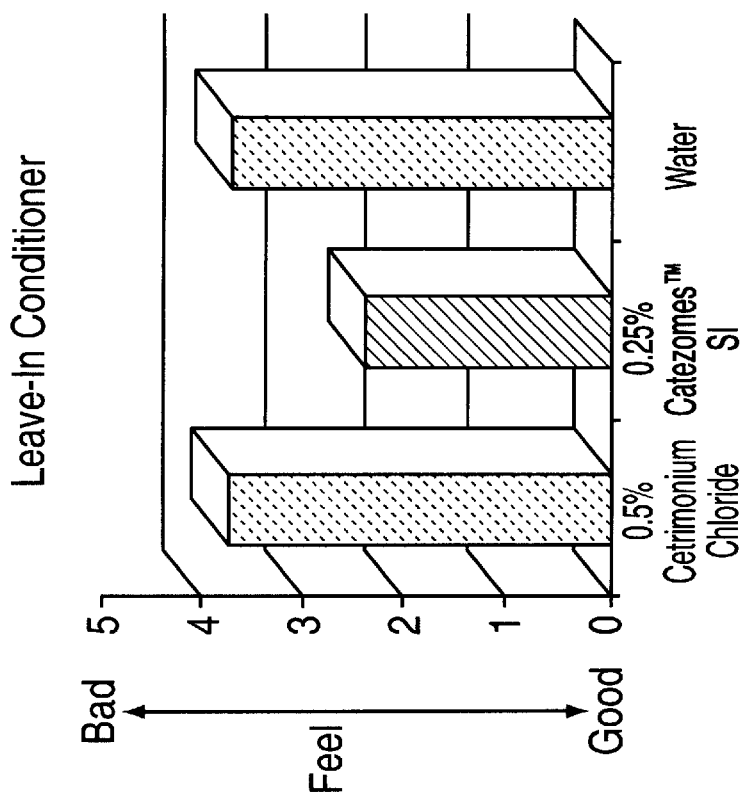
Figure 12A:
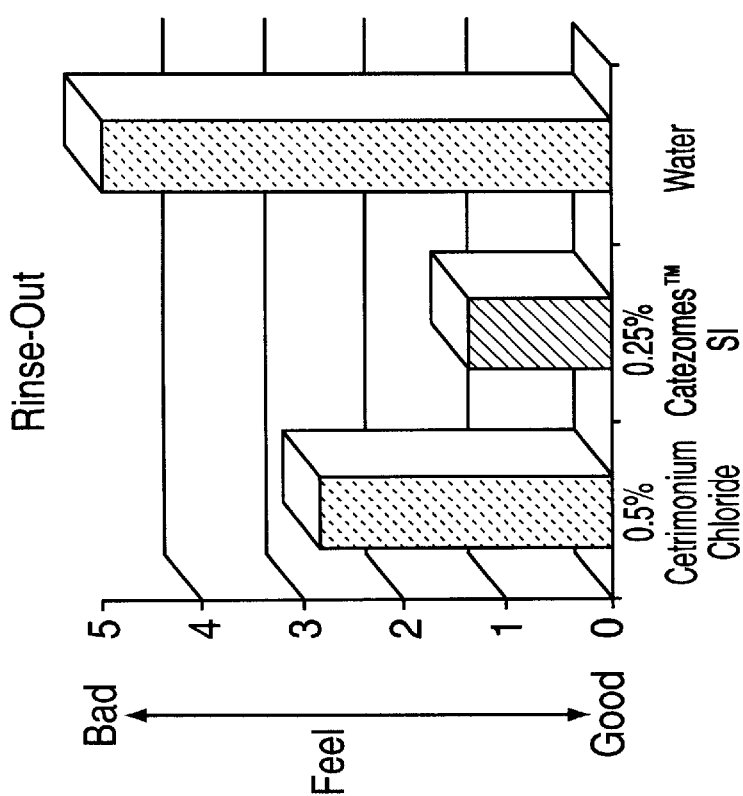

A ranking of the feel of the treated hair tresses on a scale of 1 to 5 was used, 1 being the best. FIG. 12A provides data for the tresses which were rinsed (rinse-out) and FIG. 12B provides data for the tresses which had the formulations left in (leave-in). The data show that the CATEZOMES™ SI liposomes containing 20% of the silicone hair active dimethicone improves the overall feel of the hair as compared to standard conditioning agents.

The CATEZOMES™ liposome formulations of the invention are thus ideally suited for the encapsulation of hair actives. Examples of such hair actives used to encapsulate into the liposomes of the invention include organic sunscreens, fragrances, oils, moisturizers, conditioners, and proteins e.g. enzymes, including those used in the treatment of lice infestations.

EXAMPLE 10

Figure 13A:
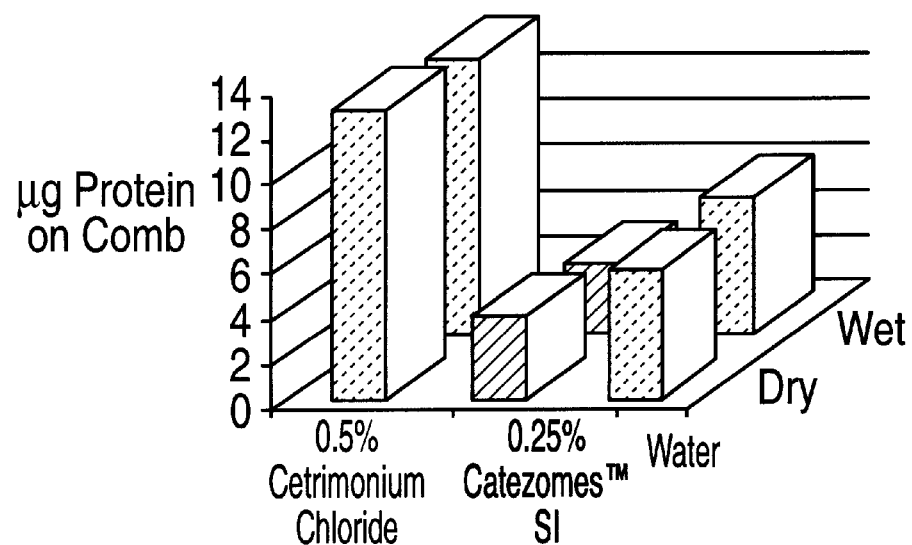
Figure 13B:
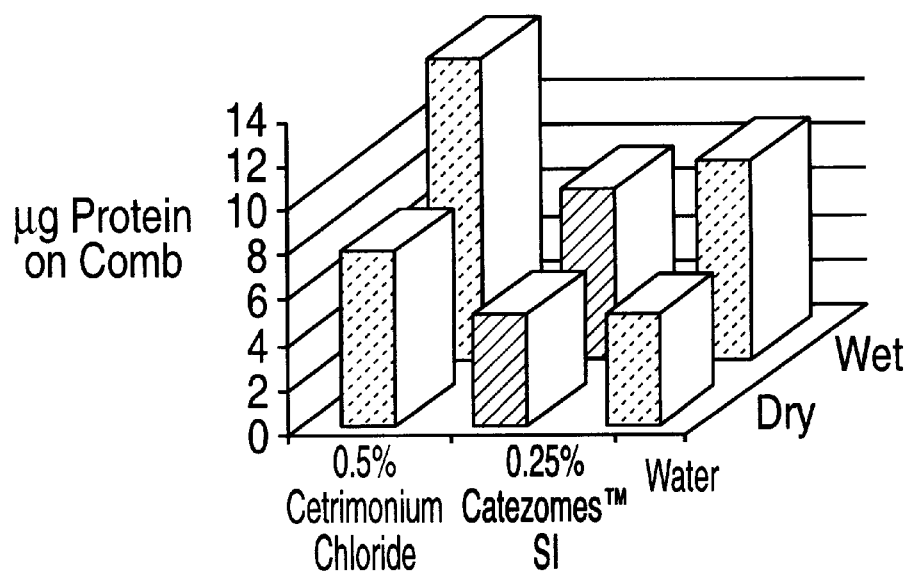

CATEZOMES™ SI liposomes of the invention produced as in Example 10 (containing 20% dimethicone) have been shown to reduce combing damage of the hair at use levels below those of other conditioning agents such as centrimonium chloride. Damage to the hair cuticle caused by combing was measured by observing the amount of protein removed during the combing process using the CATEZOMES™ SI formulation of Example 10 as compared to the centrimonium chloride formulation of Example 10. Combing damage was compared both when the hair was wet and after being dried with a household drier following either rinse-out of conditioner (FIG. 13A) or leave-in of conditioner (FIG. 13B). The data show that CATEZOMES™ SI decrease protein loss from hair at use levels below those of centrimonium chloride. Thus, the CATEZOMES™ SI protect the hair shaft.

EXAMPLE 11

Figure 14A:
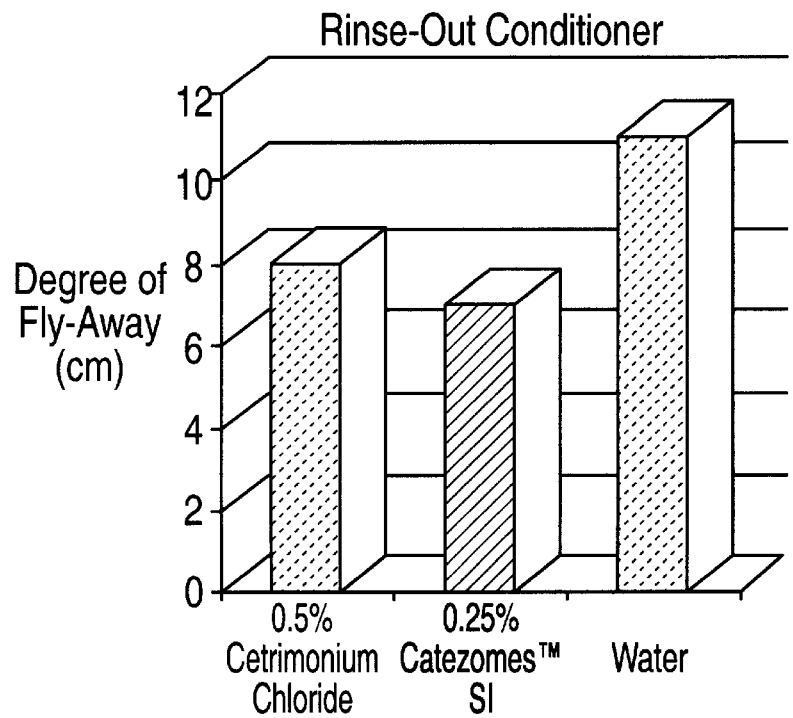
Figure 14B:
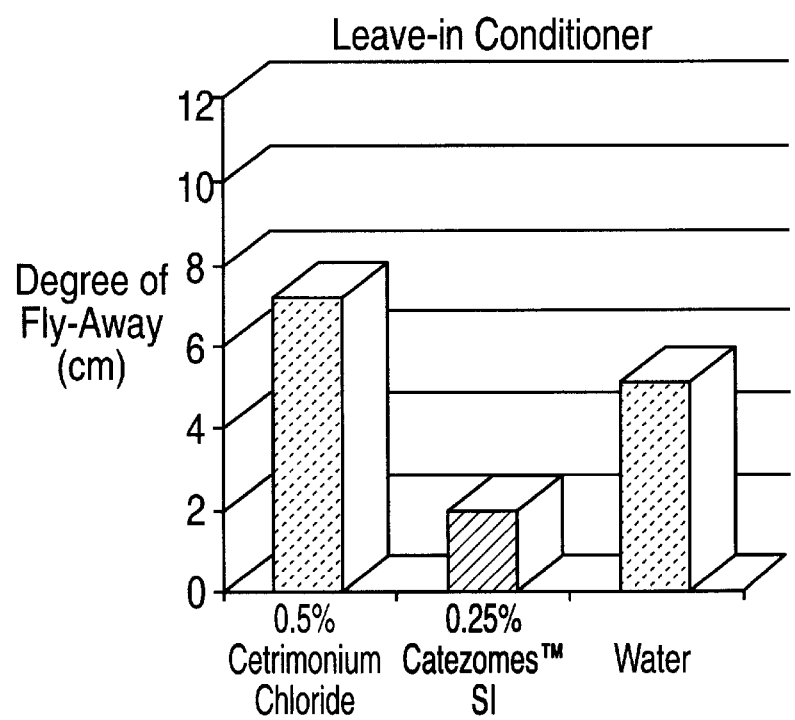

CATEZOMES™ SI liposomes of the invention produced as in Example 10 (containing 20% dimethicone) have been shown to reduce static charge on the hair at use levels below those of other conditioning agents such as centrimonium chloride. Static charge caused by combing was measured by observing the degree of spread of a hair tress following combing after using the CATEZOMES™ SI formulation of Example 10 as compared to the centrimonium chloride formulation of Example 10. Using a plastic comb, the hair tress was combed rapidly with 20 full length strokes. Following combing, the degree of spread of the hair tress was measured in centimeters for hair following rinse-out of the formulation (FIG. 14A) or leave-in of the formulation (FIG. 14B). The data show that the CATEZOMES™ SI liposomes of the invention decrease static build up on the hair and improve the manageability of hair as compared to standard conditioning agents.

What has been described herein is merely descriptive of the preferred embodiments of this invention. It is not meant in any way to limit the scope and spirt of this invention, which is only to be limited by the following claims drawn in accordance with US patent law.

What is claimed is:

1. A liposome comprising alkylammonium fatty acids salts and a load material selected from the group consisting of water, genetic material, skin actives, hair actives and fragrances, wherein said liposome is substantive to hair, tissue culture cells, epithelial cells and skin, said liposome formed by a process comprising the steps of:
    (a) dispersing long chain acyl $N_n,N_n$-dimethyl-1, n-diamino alkyl (A-ADDA) molecules and said load material in a buffering solution to form a dispersion, said buffering solution having a pH within a range of between about 3.0 to around 10.0 and an ionic strength less than or equivalent to 1 molar NaCl; and
    (b) subjecting the dispersion to high shear processing.

2. The liposome of claim 1, wherein said load material is added to said buffering solution before said A-ADDA is added.

3. The liposome of claim 1, wherein said load material is added to said buffering solution after said A-ADDA is added.

4. The liposome of claim 1, wherein said buffer solution comprises $H_2O$ and the alkylammonium fatty acid salt is trialkylammonium fatty acid salt.

5. The liposome of claim 1, wherein said step of dispersing comprises dispersing with a mechanical homogenizer.

6. The liposome of claim 1, wherein said step of dispersing is conducted at a temperature above that of the melting point of said A-ADDA.

7. The liposome of claim 1, wherein buffering solution has a pH of between about 5.5 and 10.5 and an ionic strength of less than the equivalent of 1 molar NaCl.

8. The liposome of claim 1, wherein the pH of said buffering solution is approximately 7.5.

9. The liposome of claim 1, wherein said A-ADDA is prepared from a molecule of ADDA and a fatty acid at a pH of between about 6 and 10.

10. The liposome of claim 1 wherein the genetic material is selected from the group consisting of DNA, RNA, cDNA, gDNA, mRNA, oligonucleotides, genes, gene fragments and mixtures thereof.

11. The liposome of claim 1 wherein the skin active is selected from the group consisting of water, organic sunscreens, pesticides, fragrances, oils, moisturizers, self-tanning agents, vitamin A derivatives, alpha hydroxy acids, beta hydroxy acids, topical anaesthetics, non-steroidal and steroidal anti-inflammatories, botanical extracts, proteins, capsicum, capsicum derivatives and mixtures thereof.

12. The liposome of claim 1 wherein the hair active is selected from the group consisting of water, organic sunscreens, fragrances, oils, moisturizers, conditioners, silicones, pesticides, proteins and mixtures thereof.

13. The liposome of claim 9, wherein said A-ADDA is behenyl-$N_1$-behenamido-$N_2,N_2$-dimethyl-propyl-1,3-diamine, (B-BDDP).

14. An in vivo delivery system for delivery of a load material selected from the group consisting of water, genetic material, skin actives, hair actives and fragrances, said load material first being encapsulated within a liposome formulated as in claim 1 and second being formulated into a suitable delivery vehicle.

15. The in vivo delivery system of claim 14, wherein said delivery vehicle is water.

16. The in vivo delivery system of claim 14, wherein said delivery vehicle has an ionic strength less than 1M NaCl.

17. The in vivo delivery system of claim 14, wherein the genetic material is selected from the group consisting of DNA, RNA, cDNA, gDNA, mRNA, oligonucleotides, genes, gene fragments and mixtures thereof.

18. The in vivo delivery system of claim 14, wherein the skin active is selected from the group consisting of water, organic sunscreens, pesticides, fragrances, oils, moisturizers, self-tanning agents, vitamin A derivatives, alpha hydroxy acids, beta hydroxy acids, topical anaesthetics, non-steroidal and steroidal anti-inflammatories, botanical extracts, proteins, capsicum, capsicum derivatives and mixtures thereof.

19. The in vivo delivery system of claim 14, wherein the hair active is selected from the group consisting of water, organic sunscreens, fragrances, oils, moisturizers, conditioners, silicones, pesticides, proteins and mixtures thereof.

20. A method of treating hair, comprising applying a hair active encapsulated by a liposome, wherein said liposome comprises alkylammonium fatty acids salts and wherein said hair active encapsulated by the liposome is substantive to hair, being formed by a process comprising the steps of:
    (a) dispersing long chain acyl $N_n,N_n$-dimethyl-1, n-diamino alkyl (A-ADDA) molecules and said hair active in a buffering solution to form a dispersion, said buffering solution having a pH within a range of between about 3.0 to around 10.0 and an ionic strength less than or equivalent to 1 molar NaCl; and
    (b) subjecting the dispersion to high shear processing.

21. The method of claim 20, wherein the hair active is selected from the group consisting of water, organic sunscreens, fragrances, oils, moisturizers, conditioners, silicones, pesticides, proteins and combinations thereof.

22. A method of treating skin, comprising applying a skin active encapsulated by a liposome, wherein said liposome comprises alkylammonium fatty acids salts and wherein said hair active encapsulated by the liposome is substantive to epithelial cells and skin, being formed by a process comprising the steps of:
    (a) dispersing long chain acyl $N_n,N_n$-dimethyl-1, n-diamino alkyl (A-ADDA) molecules and said hair active in a buffering solution to form a dispersion, said buffering solution having a pH within a range of between about 3.0 to around 10.0 and an ionic strength less than or equivalent to 1 molar NaCl; and (b) subjecting the dispersion to high shear processing.

23. The method of claim 22, wherein the skin active is selected from the group consisting of water, organic sunscreens, pesticides, fragrances, oils, moisturizers, self-tanning agents, vitamin A derivatives, alpha hydroxy acids, beta hydroxy acids, topical anaesthetics, non-steroidal and steroidal anti-inflammatories, botanical extracts, proteins, capsicum, capsicum derivatives and combinations of said skin actives thereof.

24. A method of delivering genetic material to tissue culture cells, other cells in culture, airway epithelial cells, and dermis cells comprising treating said cells with genetic material encapsulated by a liposome, wherein said liposome comprises alkylammonium fatty acids salts and wherein said genetic material encapsulated by the liposome is substantive to tissue culture cells, other cells in culture, airway epithelial cells, and dermis cells, being formed by a process comprising the steps of:

(a) dispersing long chain acyl $N_n,N_n$-dimethyl-1,n-diamino alkyl (A-ADDA) molecules and said genetic material in a buffering solution to form a dispersion, said buffering solution having a pH within a range of between about 3.0 to around 10.0 and an ionic strength less than or equivalent to 1 molar NaCl; and (b) subjecting the dispersion to high shear processing.

25. The method of claim 24, wherein the genetic material is selected from the group consisting of DNA, RNA, cDNA, gDNA, mRNA, oligonucleotides, genes, gene fragments and mixtures thereof.

* * * * *